United States Patent [19]

Papenfuhs

[11] 4,172,202

[45] Oct. 23, 1979

[54] PROCESS FOR THE PREPARATION OF 4-AMINO-1,8-NAPHTHALIMIDES

[75] Inventor: Theodor Papenfuhs, Frankfurt am Main, Fed. Rep. of Germany

[73] Assignee: Hoechst Aktiengesellschaft, Frankfurt am Main, Fed. Rep. of Germany

[21] Appl. No.: 867,705

[22] Filed: Jan. 9, 1978

Related U.S. Application Data

[63] Continuation of Ser. No. 649,593, Jan. 16, 1976, abandoned, which is a continuation of Ser. No. 572,754, Apr. 29, 1975, abandoned.

[51] Int. Cl.$^2$ ............................................. C07D 221/14
[52] U.S. Cl. .................................... 546/100; 544/126; 544/331; 544/332; 544/333; 544/361
[58] Field of Search ............ 260/281 S, 281 N, 281 H, 260/281 Q; 546/100; 544/126, 331, 332, 333, 361

[56] References Cited

U.S. PATENT DOCUMENTS

| | | | |
|---|---|---|---|
| 1,796,011 | 3/1931 | Eckert | 260/281 |
| 2,006,017 | 6/1935 | Eckert | 260/281 |
| 2,385,106 | 9/1945 | Scalera | 260/281 |

FOREIGN PATENT DOCUMENTS

| | | | |
|---|---|---|---|
| 42-16303 | 4/1967 | Japan | 260/281 |
| 46-07393 | 2/1971 | Japan | 260/281 |

OTHER PUBLICATIONS

Okada et al., I, Chem. Abs., 78, 148978f (1973).
Okada et al., II, Chem. Abs., 77, 76689s (1972).
Okazaki et al., Chem. Abs., 52, 337a (1956).

*Primary Examiner*—Mark L. Berch
*Attorney, Agent, or Firm*—Connolly and Hutz

[57] ABSTRACT

N-substituted amides or optionally N-substituted hydrazides of 4-amino-naphthalic acids which may be substituted in 3-position by a sulfo group are obtained by reacting 4-halo-1,8-naphthalic anhydride with a primary amine or an optionally N-substituted hydrazine having a $pK_a$-value of at least 8, exchanging in the so-obtained 4-halo-naphthalimide the halogen for the amino group by reacting it with ammonia and, optionally, subsequent sulfonation. The products are dyeing matters useful for the coloration of synthetic fibers, plastics, oils, waxes, resins, paper, printing pastes, lacquers or natural polyamides, especially for daylight-fluorescence pigments.

8 Claims, No Drawings

PROCESS FOR THE PREPARATION OF 4-AMINO-1,8-NAPHTHALIMIDES

This application is a continuation of application Ser. No. 649,593 filed Jan. 16, 1976 now abandoned which is a continuation of application Ser. No. 572,754 filed Apr. 29, 1975 and now abandoned.

The present invention relates to an improved process for the preparation of 4-amino-1,8-naphthalimide compounds.

It has been known that 4-amino-1,8-naphthalimide compounds in which only the imide nitrogen is substituted, can be prepared by nitrating acenaphthene, oxydizing the 5-nitro-acenaphthene so obtained with potassium bichromate to yield the 4-nitro-1,8-naphthalic acid anhydride, reducing the latter to give the 4-amino-1,8-naphthalic acid anhydride and subsequently reacting this compound with an aliphatic or cycloaliphatic amine, or by reacting the 4-nitro-1,8-naphthalic acid anhydride with an aliphatic amine to give the ammonium salt of the 4-nitronaphthalic acid, reducing the salt and converting it by splitting off the amine at an elevated temperature into the 4-amino-1,8-naphthalic acid-N-alkylimide into which a sulfonic acid group is then optionally introduced (cf. German Auslegeschrift No. 1 046 622 and U.S. Pat. Nos. 1 796 012, 2 474 185 and 2 715 126). These processes have the drawback that they are very complicated, and that their technical implementation is very expensive due to the use of the high-cost oxidation agent potassium bichromate and of organic solvents in the nitration and sulfonation which must be regenerated and owing to the partially very poor yields.

It has now been found that 4-amino-1,8-naphthalimide compounds of the formula I

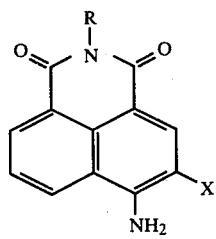
(I)

wherein R stands for an optionally substituted amino group of a hydrazine or the radical of an aliphatic, isocyclic or heterocyclic amine of the formula R—NH$_2$ having a pKa value of at least 8, and wherein X stands for a hydrogen atom or a sulfonic acid group, can be prepared in a considerably simpler way, if 1 mol of a 4-halogeno-1,8-naphthalic acid anhydride is reacted at first with 1 mol of an amine or a hydrazine of the above-specified formula R—NH$_2$ having a pKa value of at least 8 to give a compound of the formula II

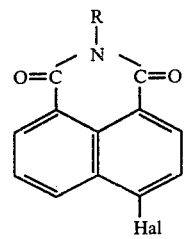
(II), wherein R has the above-mentioned meaning and Hal stands for a halogen atom, then the product is subsequently reacted with ammonia and the compound of the formula (I) thus obtained, in which X stands for a hydrogen atom, is optionally sulfonated to give the compound of the formula (I), wherein X stands for the sulfo group.

The process is carried out by heating the 4-halogeno-1,8-naphthalic acid anhydride, preferably the chloro or bromo compound, at first with the aliphatic, isocyclic or heterocyclic amine or hydrazine of the above-mentioned definition, advantageously in water, glacial acetic acid or an aprotic solvent, such as dimethylsulfoxide, N-methylpyrrolidone, phosphoric acid-tris-(N,N-dimethyl)amide or an aliphatic acid amide alkylated at the nitrogen atom, such as dimethyl-formamide or dimethylacetamide, at a temperature in the range of from 50° to 150° C., preferably from 80° to 135° C., and by reacting subsequently the N-substituted 4-halogeno-naphthalimide thus formed with ammonia in water, in aliphatic alcohols or in mixtures of the same, at a temperature in the range of from 120° to 200° C., preferably from 150° to 180° C., the reaction being carried out under pressure.

Preference is given in particular to the method of effecting both reactions in a single batch process, the 4-halogenonaphthalic acid anhydride being reacted, generally in water while adding a catalytic amount of acid, such as acetic, hydrochloric or sulfuric acid, with a mol of the organic amine or hydrazine at a temperature in the range of from 80° to 135° C., and in which process the chlorine exchange to give the substituted 4-amino-naphthalimide is effected after the imide has been formed, without isolating the intermediate product, by adding excess aqueous ammonia and increasing the temperature to a level of from 150° to 180° C.

As aliphatic amines having a pKa value of at least 8, there are to be mentioned straight-chain or branched alkylamines having from 1 to 16 carbon atoms, in particular from 2 to 6 carbon atoms, which may be substituted by hydroxy, lower alkoxy, carboxylic acid lower alkyl ester, cyano or carbonamide groups, by aromatic carbocyclic radicals, such as phenyl or naphthyl radicals, or by heterocyclic radicals of an aromatic as well as of an unsaturated and saturated nature, such as pyridine, piperidine, morpholine, pyrazole, imidazole, triazole, thiazole, thiadiazole, pyrimidine, furan, piperazine or azabicyclononane radicals, or by a primary, secondary or tertiary amino group. Here and in the following the term "lower" means aliphatic groups of 1 to 6, preferably 1 to 4 carbon atoms.

As isocyclic amines there may be mentioned, in particular, cyclo-aliphatic amines, for example, cyclohexylamine, lower alkylcyclohexylamines, halogenocyclohexylamines or cyclopentylamine which may be substituted by hydroxy, lower alkoxy, carboxylic acid lower alkyl ester, cyano or carbonamide groups or by a primary, secondary, or tertiary amino group. As heterocyclic amines there are to be mentioned, for example, aminopyridines, -pyrazoles, -imidazoles, -triazoles, -oxazoles, -thiazoles, or -pyrimidines, as well as their benzo derivatives (compounds having a fused benzene ring), these amines being required to have a pKa value of at least 8, as has been mentioned above (cf. D. D. Perrin, Dissociation Constants of Organic Bases in Aqueous Solution, London 1965).

The compounds of the formula (I), wherein X stands for a hydrogen atom and which were prepared according to the process of the invention, can be reacted in the dry state with a sulfonation agent, for example, chlorosulfonic acid, however, advantageously in low-percentage oleum (fuming sulfuric acid containing a low percentage of free sulfur trioxide), preferably with a $SO_3$ content of 5 to 20%, at a temperature not exceeding 50° C., preferably in a range of from 15° to 40° C., to give the corresponding 3-sulfo-4-amino-1,8-naphthalic acid amide compounds.

If the sulfonation is effected in a solvent, the dyestuff precipitates as a rule as a salt-free compound and can be isolated easily by being filtered off and subsequently washed with a solvent. As a rule, the yields exceed 95% of the theoretical yield. After the sulfonation in oleum, the reaction solution is poured into water, while cooling, and the water-soluble product is salted out.

The compounds of the formula (I), wherein X stands for a hydrogen atom and wherein R does not contain sulfo groups, which can be obtained according to the invention, represent water-insoluble dyestuffs which are suitable for the dyeing and printing of synthetic fibers, for example on the basis of polyacrylonitrile or copolymers of acrylonitrile with other vinyl compounds, such as acrylic esters, acrylamides, vinyl pyridine, vinyl chloride or vinylidene chloride, or of copolymers from dicyanoethylene and vinyl acetate, as well as of acrylonitrile block copolymers, fibers on the basis of polyurethanes, polypropylene, cellulose tri- and 2½-acetate and in particular fibers on the basis of polyamides, such as polyamide-6, polyamide-6,6 or polyamide-12 and of aromatic polyesters, as those of terephthalic acid and ethylene-glycol or 1,4-dimethylolcyclohexane, and copolymers of terephthalic and isophthalic acid and ethylene glycol. The said dyestuffs yield yellow dyeings of an intensive fluorescence and a good color intensity (tinctorial strength) as well as a high brilliancy, which have an excellent fastness to high temperatures and partially also a good fastness to light and wetting.

They are also suitable for the dyeing in the mass of plastic materials, resins, oils, waxes and paper, as well as for printing inks, paints and lacquers and also for the spin dyeing of polyacrylonitrile. They are particularly suitable for the preparation of pigments fluorescent in daylight.

The compounds to be obtained according to the invention which have the formula (I), wherein X represents a sulfonic acid group or the radical R contains a sulfonic acid group, are water-soluble and are suitable for the dyeing of natural and synthetic polyamide fibers, such as wool or polyamide fibers on the basis of adipic acid and hexamethylene diamine or xylylene diamine, aminoundecanoic acid or -dodecanoic acid, ε-caprolactam, butyrolactam, aminopelargonic acid or amino-enanthic acid, according to the common dyeing processes, while yielding greenish yellow color shades of an excellent brilliancy, the dyeings having sufficient fastness properties.

Of the compounds corresponding to the formula (I) which can be prepared according to the invention, particularly those compounds can be obtained in an especially easy way and with a high degree of purity, in which R stands for an alkyl radical having 1 to 4 carbon atoms, which is straight-chained or branched and which may be substituted by alkoxy groups having preferably 1 to 4 carbon atoms, or by hydroxy, phenyl and/or primary, secondary or tertiary amino groups, which amino groups, for example, are optionally substituted by alkyl radicals having 1 to 4 carbon atoms which may further contain hydroxy or alkoxy groups of 1 to 4 carbon atoms, or phenyl radicals, and/or which said amino groups are substituted by phenyl or benzyl radicals; or R stands for the amino group which may also be substituted by alkyl groups having 1 to 4 carbon atoms or by phenyl radicals.

The following Examples serve to illustrate the invention. The parts are parts by weight, the percentages of solutions or mixtures are percent by weight. Parts by weight and parts by volume are in the same ratio as the kilogram to the liter.

EXAMPLE 1

348.8 Parts of 4-chloronaphthalic acid anhydride were introduced into 1200 parts of glacial acetic acid, 122 parts of methylamine solution of 40% strength were added dropwise, and the mixture was then heated under reflux for 12 hours. Subsequently the reaction mixture was cooled, was suction-filtered, washed with glacial acetic acid, then with water and dried.

320 Parts (87% of the theory) of 4-chloronaphthalic acid-N-methylimide were obtained which had the formula

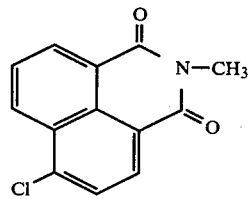

which product was homogeneous and which did not contain any impurities according to the chloroanalysis and the chromatogram.

123 Parts of this compound were heated in an autoclave, while adding catalytic amounts of copper powder, with 512 parts of aqueous ammonia of about 25% strength for 8 hours at a temperature of 170° C., in which process a pressure of about 30 atmospheres gage was established. Subsequently the mixture was cooled, the pressure was released, the product was suction-filtered, washed with water until neutral and dried.

107 Parts (95% of the theory) of 4-amino-naphthalic acid-N-methylimide were obtained which had the formula

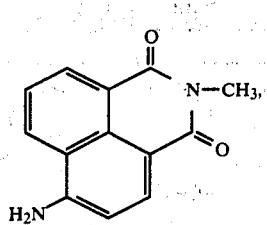

in the form of a yellow dyestuff with a green fluorescence which was able to dye polyester in brilliant shades.

EXAMPLE 2

116.3 Parts of 4-chloronaphthalic acid anhydride were heated in an autoclave for 8 hours at 170° C. (pressure about 6 atmospheres gage), together with 1400 parts of water, 40 parts of glacial acetic acid and 32.4 parts of monoethanolamine.

To the suspension of the 4-chloronaphthalic acid-N-β-hydroxethylimide thus prepared which had the formula

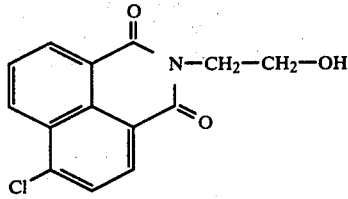

without isolation 300 parts of gaseous ammonia were added and the mixture was then maintained at 170° C. for another 8 hours (pressure about 30 atmospheres gage). Thereafter, the reaction mixture was cooled, the pressure was released, and the product was suction-filtered, washed until neutral and dried. 125.4 Parts (98% of the theory) of 4-amino-naphthalic acid-N-β-hydroxethylimide were obtained which had the formula

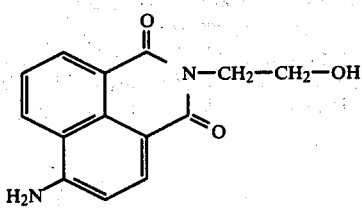

and which was suitable in particular for the preparation of luminescent pigments fluorescent at daylight on the basis of melamine/formaldehyde/toluene-sulfonamide and yielded strongly greenish yellow dyeings of a good color intensity, which had good fastness properties.

EXAMPLES 3 to 12

When in the reaction of the 4-chloronaphthalic acid anhydride, corresponding amounts of the amines specified in the following Table 1 were used instead of methylamine or monoethanolamine, and the reaction with ammonia was carried out subsequently according to the method described in Examples 1 and 2, further greenish yellow dyestuffs according to the invention were obtained, which had the general formula

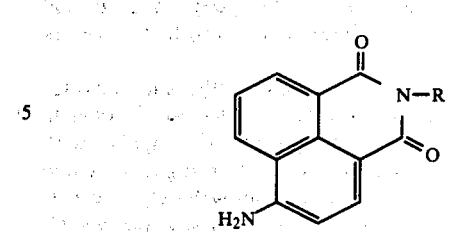

and which could be used advantageously in the above-mentioned fields of application. The dyestuff yields are shown in the following Table.

Table 1

| Example | R= | Yield |
|---|---|---|
| 3 | n—C$_4$H$_9$ | 96.5 % |
| 4 | —CH$_2$—(phenyl) | 98.5 % |
| 5 | —CH$_2$—CH$_2$—(phenyl) | 98.5 % |
| 6 | —(CH$_2$)$_3$—OCH$_3$ | 94.0 % |
| 7 | —NH$_2$ | 97.5 % |
| 8 | —(cyclohexyl)H | 93.5 % |
| 9 | —CH(CH$_3$)$_2$ | 92.5 % |
| 10 | —CH$_2$—CHOH—CH$_2$OH | 98.0 % |
| 11 | —(cyclopentyl with CH$_3$)H | 92.5 % |
| 12 | (imidazolyl —N=CH—N—NH) | 95.0 % |

EXAMPLE 13

277 Parts of 4-bromonaphthalic acid anhydride were suspended in 2200 parts of water and were heated to the boil, while stirring, after 20 parts of formic acid had been added. Subsequently a 10% aqueous solution of 205 parts of 3-di-n-butylaminopropylamine was added dropwise during 6 hours. The reaction mixture was then stirred for another 10 hours and, after cooling to 20° C., the substituted 4-bromonaphthalimide formed which had the formula

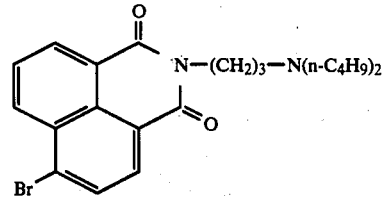

was suction-filtered, was washed until neutral and dried. 409 Parts of this intermediate product were obtained.

22.25 Parts of the 4-bromonaphthalic acid-(3-dibutylaminopropyl)-imide were heated for 9 hours in the autoclave at a temperature of 150° C., together with 250 parts ethanolic ammonia of 15% strength, in which process a pressure of about 25 atmospheres gage was established. Subsequently the reaction mixture was allowed to cool, the pressure was released, 750 parts of water were added, and the dyestuff formed which had the formula

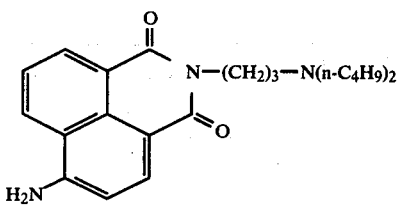

was suction-filtered, was washed with water until neutral and dried. 20 Parts of a dyestuff were obtained which yielded greenish yellow dyeings with good fastness properties in the above-mentioned fields of application.

EXAMPLES 14 to 24

If instead of dibutylaminopropylamine, aliquot amounts of the diamines specified in Table 2 were used, and the subsequent reaction with ammonia was carried out according to the method described in Example 13, dyestuffs according to the invention were also obtained in the specified yields, which corresponded to the general formula

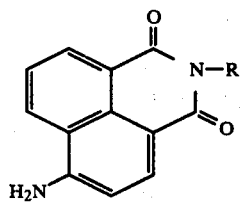

which could be used in the same manner.

Table 2

| Example | R= | Yield |
|---|---|---|
| 14 | —CH$_2$—CH$_2$—[cyclohexyl-H]—CH$_2$—CH$_2$—NH$_2$ | 91.0 % |
| 15 | —(CH$_2$)$_4$—NH$_2$ | 84.5 % |
| 16 | —(CH$_2$)$_3$—N(CH$_2$—[cyclohexyl-H]—CH$_2$) | 93.5 % |
| 17 | —(CH$_2$)$_3$—N(morpholino) | 95.5 % |
| 18 | —(CH$_2$)$_3$—N(CH$_2$—CH$_2$—OH)$_2$ | 90.0 % |
| 19 | —CH$_2$—[phenyl]—CH$_2$—NH$_2$ | 98.5 % |
| 20 | —[cyclohexyl-H]—C(CH$_3$)$_2$—[cyclohexyl-H]—NH$_2$ | 94.7 % |
| 21 | —(CH$_2$)$_3$—NH—C$_2$H$_5$ | 91.5 % |
| 22 | —[cyclohexyl-H]—CH$_2$—[cyclohexyl-H]—NH$_2$ | 95.0 % |
| 23 | —CH$_2$—[phenyl]—CH$_2$—NH$_2$ | 97.0 % |
| 24 | —CH$_2$—C(CH$_3$)$_2$—NH$_2$ | 86.5 % |

46.5 Parts of 4-chloronaphthalic acid anhydride, 27.9 parts of m-xylylene-diamine, 20 parts of glacial acetic acid and 450 parts of water were heated for 10 hours in an autoclave at a temperature in the range of from 130° to 140° C. (pressure about 4 atmospheres gage). After cooling, the pressure was released, the product was suction-filtered, was washed with water until neutral and dried. 69 Parts (98.4% of the theory) of a dyestuff precursor were obtained which had the following formula

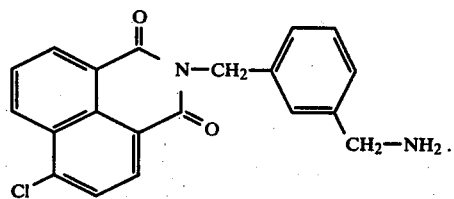

35.1 Parts of this compound were heated for 6 hours at a temperature of 180° C., together with 400 parts of aqueous ammonia of 20% strength, after catalytic amounts of copper powder had been added, in which process a pressure of about 40 atmospheres gage was established. Subsequently the reaction mixture was cooled, the pressure was released, the product was suction-filtered, was washed until neutral and dried. The dyestuff thus isolated which had the formula

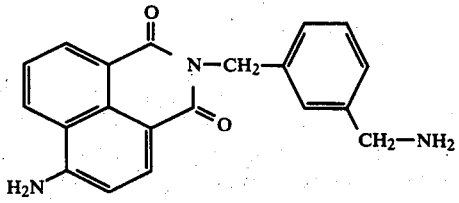

was obtained in the form of an analytically pure product with a yield of 95% (31.5 parts). It could be used preferably for the preparation of greenish yellow daylight-fluorescence pigments.

EXAMPLE 26

232.5 Parts of 4-chloronaphthalic acid anhydride, 89 parts of 5-amino-1,2,4-triazole and 750 parts of N-methylpyrrolidone were heated for 5 hours at 130° C. The reaction mixture was then cooled to 60° C., diluted with 1000 parts of methanol and cooled to room temperature. The precipitated 4-chloronaphthalic acid-triazolylimide of the formula

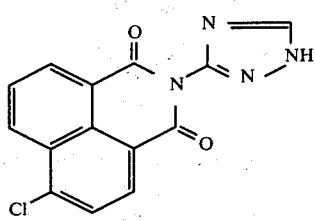

was suction-filtered, was washed with methanol and then with water and dried. 281 Parts of dyestuff precursor were obtained.

29.9 Parts of this compound were heated with 300 parts of isopropanolic ammonia of 17% strength in an autoclave during 12 hours at a temperature in the range of 140° to 145° C. After cooling the pressure was released, and the precipitated product of the formula

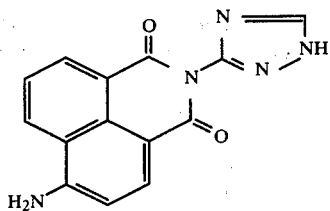

was suction-filtered, was washed with isopropanol and then with water and was dried. 26.8 Parts (96% of the theory) of dyestuff were obtained which—when finely dispersed according to known methods—was able to dye polyester in very brilliant greenish yellow color shades, which dyeings had good fastness properties.

EXAMPLE 27

22.6 Parts of 4-aminonaphthalic acid methylimide prepared according to Example 1 were introduced into 110 parts of oleum of 20% strength during 2 hours, at room temperature, while stirring. The mixture was heated at a temperature in the range of 45° to 50° C. and was maintained in this range until a drop test was clearly soluble in water (30 to 120 minutes).

Subsequently the mixture was poured into 660 parts of water (final temperature about 60° C.), the solution was heated to 90° C., was filtered after 3 parts of active charcoal had been added, and the product was salted out from the filtrate at 50° C. with 80 parts of sodium chloride. After cooling the reaction mixture was filtered, was washed until neutral with sodium chloride solution of 10% strength and was dried.

34.4 Parts of a dyestuff of 77.5% strength were obtained which had the formula

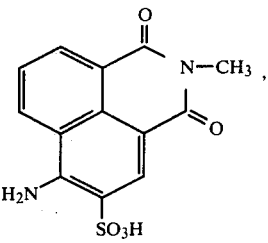

and which dyed fibers on the basis of natural and synthetic polyamide in excellently brilliant greenish yellow color shades with good fastness properties. The dyestuff is also extremely suitable for obtaining clear green shades.

EXAMPLE 28

128 Parts of 4-aminonaphthalic acid-N-$\beta$-hydroxethylimide prepared according to Example 2 were dissolved in 1500 parts of chlorobenzene at 40° C. Subsequently 128 parts of chlorosulfonic acid were added dropwise during 3 hours, and the reaction mixture was then stirred for 10 hours at a temperature in the range of 35° to 40° C. The precipitated dyestuff of the formula

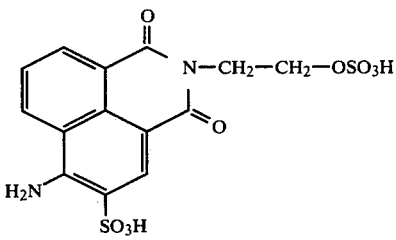

was suction-filtered, washed with chlorobenzene and then with methylene chloride and dried. 204 Parts (98% of the theory) of a salt-free product were obtained which was capable to dye wool and synthetic polyamides in fluorescent greenish yellow color shades with a good fastness.

EXAMPLES 29 to 35

If aliquot parts of the 4-aminonaphthalimides described in Examples 3 and 6 to 11 were used for the reaction according to Example 27, instead of 4-aminonaphthalic acid-methylimide, and the said products were sulfonated according to the described method, comparable acid dyestuffs were isolated which had the general formula

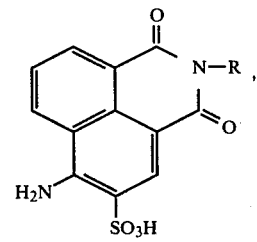

the meaning of radical R becoming evident from Table 4 below.

Table 4

| Example | R= | Yield |
|---------|----|----|
| 29 | —n—C₄H₉ | 89.5 % |
| 30 | —(CH₂)₃—OCH₃ | 92.0 % |
| 31 | —C₂H₅ | 90.4 % |
| 32 | —⟨cyclohexyl-H⟩ | 92.0 % |
| 33 | —CH(CH₃)CH₃ | 85.7 % |
| 34 | —CH₂—CHOH—CH₂OH | 81.8 % |
| 35 | —⟨methylcyclohexyl-H⟩ | 94.1 % |

EXAMPLES 36 to 38

If in Example 28 the 4-aminonaphthalic acid-N-β-hydroxethylimide was replaced by corresponding amounts of the 4-aminonaphthalimides described in Examples 4, 5 and 12 (Table 1) and the reaction was carried out accordingly, dyestuffs in conformance with the invention which had the general formula

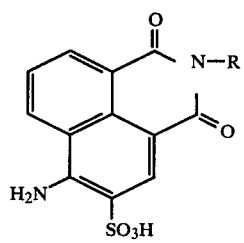

(meaning of R cf. Table 5 below) were also obtained in a comparable quality and yield, which dyed natural and synthetic polyamides in brilliant greenish yellow shades with a good fastness.

Table 5

| Example | R= | Yield |
|---------|----|----|
| 36 | —CH₂—phenyl | 94.5 % |
| 37 | —CH₂—CH₂—phenyl | 96.2 % |
| 38 | —⟨imidazolyl N=…N—NH⟩ | 89.7 % |

I claim:

1. In a process for the preparation of a compound of the formula I

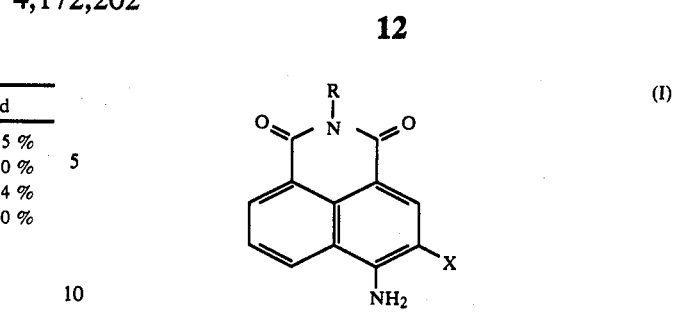

in which R is amino, alkyl of 1 to 16 carbon atoms, alkyl of 1 to 16 carbon atoms substituted by hydroxy, lower alkoxy, carboxylic acid lower alkyl ester, cyano, carbonamido, phenyl, naphthyl, pyridyl, piperidinyl, morpholinyl, pyrazolyl, imidazolyl, triazolyl, thiazolyl, thiadiazolyl, pyrimidinyl, furyl, piperazinyl or azabicyclononyl, or is cyclohexyl, lower-alkylcyclohexyl, halogeno-cyclohexyl, cyclopentyl, pyridyl, pyrazolyl, imidazolyl, triazolyl, oxazolyl, thiazolyl or pyrimidinyl, said R deriving from a compound R—NH₂ having a pKa value of at least 8, and X is hydrogen or sulfo, starting from a 4-halo-1,8-naphthalic acid anhydride and reacting it with an amino compound, the improvement consisting of using as a reactant with the 4-halo-1,8-naphthalic acid anhydride an amino compound of the formula R—NH₂ of a pKa-value of at least 8, R being defined as above, and reacting at 150°–180° C. in water the so-obtained compound of the formula II

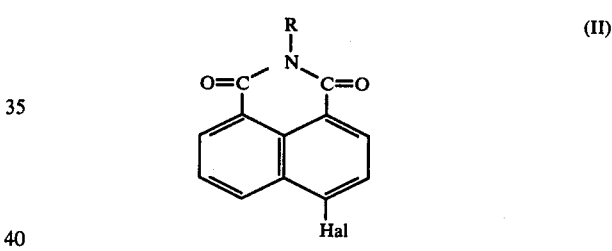

in which Hal stands for halogen and R is defined as above, with ammonia and, optionally, sulfonating the so-obtained compound of formula I in which X is hydrogen to yield the corresponding compound in which X is sulfo.

2. In a process for the preparation of a compound of the formula I

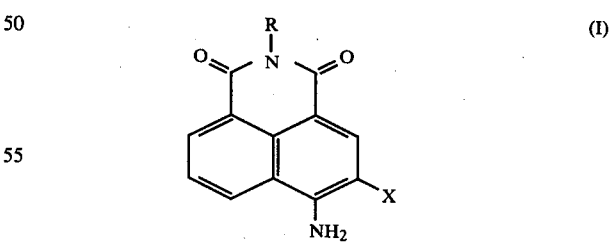

in which R is amino, alkyl of 1 to 16 carbon atoms, alkyl of 1 to 16 carbon atoms substituted by hydroxy, lower alkoxy, carboxylic acid lower alkyl ester, cyano, carbonamido, phenyl, naphthyl, or is cyclohexyl, lower-aklylcyclohexyl, halogeno-cyclohexyl, cyclopentyl, pyridyl, pyrazolyl, imidazolyl, triazolyl, oxazolyl, thiazolyl or pyrimidinyl, said R deriving from a compound R—NH₂ having a pKa value of at least 8, and X is hydrogen or sulfo, starting from a 4-halo-1,8-naphthalic acid anhydride and reacting it with an amino compound, the improvement consisting of using as a reactant with the 4-halo-1,8-naphthalic acid anhydride an amino compound of the formula R—NH$_2$ of a pKa-value of at least 8, R being defined as above, and reacting at 150°–180° C. in water the so-obtained compound of the formula II

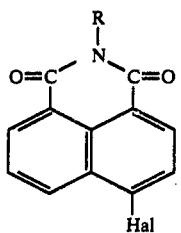

(II)

in which Hal stands for halogen and R is defined as above, with ammonia and, optionally, sulfonating the so-obtained compound of formula I in which X is hydrogen to yield the corresponding compound in which X is sulfo.

3. In a process for the preparation of a compound of the formula I

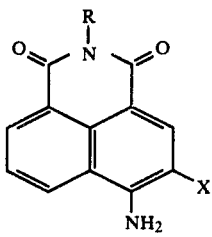

(I)

in which R is alkyl of 1 to 4 carbon atoms which alkyl is unsubstituted or substituted by alkoxy of 1 to 4 carbon atoms, hydroxy phenyl or amino which amino is unsubstituted or substituted by phenyl, benzyl or alkyl of 1 to 4 carbon atoms said alkyl in turn being unsubstituted or substituted by hydroxy, alkoxy of 1 to 4 carbon atoms or phenyl, or R is amino or amino substituted by alkyl of 1 to 4 carbon atoms or phenyl, said R deriving from a compound R—NH$_2$ having a pKa value of at least 8, and X is hydrogen or sulfo, starting from a 4-halo-1,8-naphthalic acid anhydride and reacting it with an amino compound, the improvement consisting of using as a reactant with the 4-halo-1,8-naphthalic acid anhydride an amino compound of the formula R—NH$_2$ of a pKa-value of at least 8, R being defined as above, and reacting at 150°–180° C. in water the so-obtained compound of the formula II

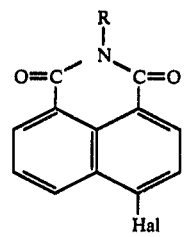

(II)

in which Hal stands for halogen and R is defined as above, with ammonia and, optionally, sulfonating the so-obtained compound of formula I in which X is hydrogen to yield the corresponding compound in which X is sulfo.

4. A process as claimed in claim 1, wherein Hal is chlorine or bromine.

5. A process as claimed in claim 1, wherein the 4-halo-naphthalic anhydride is reacted in water with catalytic amounts of an acid with the stoichiometric amount of the compound of the formula R—NH$_2$ at a temperature of 80° to 135° C. and without intermediate isolation the compound of the formula II is reacted with an excess of aqueous ammonia at a temperature of 150° to 180° C.

6. A process as claimed in claim 1, wherein sulfonation is performed by reacting the dry compound in which X is hydrogen with chlorosulfonic acid or fuming sulfuric acid containing up to 20% of free sulfur trioxide at a temperature not exceeding 50° C.

7. A process as claimed in claim 6, wherein the fuming sulfuric acid contains 5 to 20% of free sulfur trioxide.

8. A process as claimed in claim 6, wherein the temperature is 15° to 40° C.

* * * * *